United States Patent [19]
Oei

[11] Patent Number: 5,120,538
[45] Date of Patent: Jun. 9, 1992

[54] COMBINATIONS OF COMPOUNDS ISOLATED FROM CURCUMA SPP AS ANTI-INFLAMMATORY AGENTS

[75] Inventor: Ban Liang Oei, Bandung, Indonesia

[73] Assignee: PT Darya-Varia Laboratoria, Jakarta, Indonesia

[21] Appl. No.: 474,974

[22] Filed: Feb. 5, 1990

[51] Int. Cl.$^5$ .................. A61K 35/78; A61K 31/425; A01N 43/78
[52] U.S. Cl. ................ 424/195.1; 514/365; 514/783
[58] Field of Search ............ 424/195.1; 514/365, 514/783

[56] References Cited

U.S. PATENT DOCUMENTS 4,810,716  3/1989  Connor et al. ............ 514/365
4,959,503  9/1990  Connor et al. ............ 564/265

FOREIGN PATENT DOCUMENTS 149242  12/1983  European Pat. Off. ............ 31/15
2924345  1/1981  Fed. Rep. of Germany .

OTHER PUBLICATIONS

Garg, *Planta Medica*, 26:225-227 (1974).
E. Gunther, *The Essential Oils*, pp. 120-126 (1955).
*Hangers Hand buch der Pharmazeutischen Praxis*, vol. 4, p. 386, 4th ed. (1973).
Herisset et al., *Plantes Medicinales et Phytotherapie*, 6:281-291 (1972).
Isaac, *Pharmazeutische Zeitung*, 104:860-864 (1959).
Janaki and Bose, *J. Ind. Chem. Soc.*, 44:985-986 (1967).
Jentzsch et al., *Pharmaceutica Acta Helvetiae*, 34:181-186 (1959).
Jentzsch et al., *Sci. Pharm.*, 36:251-257 (1968).
Jentzsch et al., *Sci. Pharm.*, 38:50-58 (1970).
Luckner et al., *Pharmazie*, 22:371-375 (1967).
Lutomski et al., *Planta Medica*, 26:9-19 (1974).
Malingre, *Pharmaceutisch Weekblad*, 110:601-610 (1975).
Makerji et al., *J. Sci. Industr. Res.*, 20C:25-28 (1961).
Ramprasad and Sirsi, *J. Sci. Industr. Res.*, 15C:239-241 (1956).
Ramprasad and Sirsi, *J. Sci. Industr. Res.*, 15C:262-265 (1956).
Ramprasad and Sirsi, *J. Sci. Industr. Res.*, 15C:136-143 (1957).
Rao et al., *J. Nutrition*, 100:1307-1316 (1980).
Srimal and Dhawan, *J. Pharm. Pharmac.*, 25:447-452 (1973).
Su et al., *J. Agric. Food Chem.*, 30:290-292 (1982).
*Drug Analaysis by Chromatography and Microscopy*, p. 169 (1973).
Chem. Abstracts vol. 61 1788 1964.

*Primary Examiner*—Johnnie R. Brown
*Assistant Examiner*—Ralph G. Tomer
*Attorney, Agent, or Firm*—Townsend and Townsend

[57] ABSTRACT

This invention relates to naturally occurring pharmaceutical compositions, more particularly, those compositions of compounds isolated from the plant genus, Curcuma, which are useful as anti-inflammatory agents.

14 Claims, No Drawings

COMBINATIONS OF COMPOUNDS ISOLATED FROM CURCUMA SPP AS ANTI-INFLAMMATORY AGENTS

BACKGROUND OF THE INVENTION

1. Field of the Invention

This invention relates to naturally occurring pharmaceutical compositions, more particularly, compositions of compounds isolated from the plant genus, Curcuma, which are useful as anti-inflammatory agents.

2. Information Disclosure

Curcumin and essential oils isolated from *Curcuma longa* are known to be useful for gastrointestinal disorders. Ramprasad and Sirsi, *Studies On Indian Medicinal Plants: Curcuma Longa—Effect Of Curcumin And The Essential Oils Of C. Longa On Biosecretion*, J. Sci. Industr. Res. 15C:262-265 (1956); Ramprasad and Sirsi, *Observations on the Pharmacology of Curcuma Longa*, J. Sci. Industr. Res. 15C:136-143 (1957); Mukerji, et al., *Spices & Gastric Function: Part I-Effect of Curcuma Longa on the Gastric Secretion in Rabbits*, J. Sci. Industr. Res. 20C:25-28 (1961). The same compounds are also known to have antibacterial activity. Ramprasad and Sirsi, *Studies On Indian Medicinal Plants: Curcuma Longa—In vitro Bacterial Activity Of Curcumin And The Essential Oil*, J. Sci. Industr. Res. 15C:238-241 (1956). Two compounds isolated from *C. longa* have been shown to be effective insect repellents. Su, et al., *Isolation, Purification, and Characterization of Insect Repellents from Curcuma longa*, J. Agric. Food Chem. 30:290-292 (1982). Curcumin has also been shown to lower cholesterol levels in rats. Rao, et al., *Effect Of Curcumin On Serum And Liver Cholesterol Levels In The Rat*, J. Nutrition, 100:1307-1316 (1980). Extracts of the rhizome (underground stem) show 100% antifertility activity on rats. Garg, *Effect of Curcuma Longa (Rhizomes) on Fertility in Experimental Animals*, Planta Medica, 26:225-227 (1974). The anti-inflammatory effects of curcumin isolated from *Curcuma longa* are also known. Srimal and Dhawan, *Pharmacology of Diferuloyl Methane, a Non-steroidal Anti-inflammatory Agent*, J. Pharm. Pharmac. 25:447-452 (1973).

The yellow pigment of the rhizome of *C. longa* is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane). *Drug Analysis by Chromatography and Microscopy*, p. 169 (Ann Arbor Science Inc., 1973). Bis-desmethoxycurcumin is known to inhibit the choleretic effect of curcumin. Jentzsch et al., *Pharmaceutica Acta Helvetiae*, 34:181 (1959). Methods for preparing curcuminoids are known. Janaki and Bose, *An Improved Method for the Isolation of Curcumin From Turmeric*, J. Indian Chem. Soc. 44:985 (1967).

The essential oils of *C. domestica* and *C. xanthorrhiza* are primarily composed of the following compounds: d-Camphor (1%), Cyclo-isoprenemyrcene (85%), and p-Tolylmethylcarbinol (5%). E. Gunther, *The Essential Oil*, p. 123-4 (Van Nostrand Co., 1955).

SUMMARY OF THE INVENTION

This invention provides for a method for potentiating the anti-inflammatory effect of curcuminoids by substantially removing bis-desmethoxycurcumin from the other curcuminoids and by adding essential oils extracted from tissues of *Curcuma domestica* or *Curcuma xanthorrhiza* or a combination of both oils. By "substantially removing" it is meant that the amount of bis-desmethoxycurcumin remaining has no biologically detectable effect on the anti-inflammatory potency of the composition.

The proportion of essential oil of *C. domestica* to essential oil of *C. xanthorrhiza* to curcuminoids is preferably in a range of approximately 5-15:2-7.5:1, respectively. It is particularly preferred that the range of proportions is 7.5-10:2.5-5:1. In general, it is preferred that the proportion of the essential oil of *C. domestica* is about twice the proportion of *C. xanthorrhiza*.

This invention also provides for a method of treating inflammation by administering an effective dose of a pharmaceutical composition comprising curcuminoids, substantially free of bis-desmethoxycurcumin, and essential oils extracted from tissues of *C. domestica* or *Curcuma xanthorrhiza* or a combination of both oils. By "substantially free" it is meant that the amount of bis-desmethoxycurcumin remaining has no biologically detectable effect on the potency of the composition. Preferred pharmaceutical compositions comprise combinations and proportions of curcuminoids and essential oils as provided above.

This invention also provides for a method wherein the disclosed pharmaceutical composition are administered via an oral dosage.

This invention further relates to a pharmaceutical composition comprising active ingredients of curcuminoids, substantially free of bis-desmethoxycurcumin, and essential oils extracted from tissues of *C. domestica* or *C. xanthorrhiza* or a combination of both oils and a pharmaceutical carrier. Preferred compositions comprise combinations and proportions of curcuminoids and essential oils as provided above.

This invention also relates to a composition wherein the pharmaceutical carrier comprises pharmaceutical excipients suitable for oral administration. It is preferred that the excipients comprise either a soft capsule or a solution suitable for drinking.

DETAILED DESCRIPTION OF THE PREFERRED EMBODIMENTS

This invention provides for pharmaceutical compositions comprising curcuminoids, substantially free of bis-desmethoxycurcumin, and the essential oils of *C. domestica* or *C. xanthorrhiza* or a combination of both oils and methods for using the same.

Turmeric, *Curcuma domestica* (also known as *C. longa*), is a tropical herb of the Zingiberaceae family indigenous to Southern Asia. The aromatic yellow powder from its mature rhizomes has been used in Asian countries as a yellow vegetable dye for silks and cottons. It is also used in foods as a condiment, particularly as an essential ingredient of curry powder. In medicine, it is used for gastrointestinal disorders.

The strong coloring pigment in turmeric contains three compounds known as curcuminoids. They are: curcumin (diferuloylmethane), desmethoxycurcumin (hydroxycinnamoyl feruloylmethane), and bis-desmethoxycurcumin (dihydroxydicinnamoyl methane).

The essential oils of *C. domestica* and *C. xanthorrhiza* are prepared by steam distilling dried rhizomes (underground stems). The major constituents of the essential oils are: D-Camphor (1%), Cyclo-isoprenemyrcene (85%), and P-Tolylmethylcarbinol (5%).

The anti-inflammatory effects of curcumin are known. Srimal and Dhawan, (1973). Bis-desmethoxycurcumin, however, is also known to inhibit the choleretic effect of curcumin. Jentzsch et al., (1959). In order to enhance the anti-inflammatory properties of the composition in the present invention, a method for separating bis-desmethoxycurcumin from curcumin on a preparative scale has been developed. Hereinafter, use of the term "curcuminoids" will refer to a preparation of curcuminoids from which bis-desmethoxycurcumin has been substantially removed.

C. domestica or C. xanthorrhiza rhizomes are cut into slices, dried and powdered. The essential oils are extracted from the powder by imbibing with one liter of petroleum-ether (Pae) for every kilogram of powder. After imbibing overnight, liquid is pressed out of the powder under a pressure of 400 atm. The pressing step is repeated several times until the liquid contains no more oil. The Pae is evaporated off and the residual essential oil is steam distilled.

To isolate the curcuminoids, the rhizome residue after Pae extraction is then extracted with alcohol in the same manner. The alcohol is evaporated off and the residue is recrystalized.

The bis-desmethoxycurcumin is separated from the other curcuminoids by flash chromatography using a silica gel (230-400 mesh) column. First, benzene is used to elute most of the curcumin from the column. Next, a mixture of benzene and alcohol (99.5:1, respectively) is used to elute desmethoxycurcumin from the column. The bis-desmethoxycurcumin remains in the column after these two elution steps.

According to the present invention, it has been found that the combination of curcuminoids, the essential oils of C. domestica and the essential oils of C. xanthorrhiza have anti-inflammatory effects comparable to piroxicam, a known anti-inflammatory agent. The combination has higher activity than that expected from the mixture of the components. The anti-inflammatory effects of the essential oils and their synergistic interaction with curcumin has not been previously described. The administration of the combination is to be an effective method of treating muscle soreness, backpain, joint discomforts, arthritis and other inflammatory conditions.

The present invention provides a pharmaceutical composition for controlling inflammation, having active ingredients of curcuminoids, the essential oils of C. domestica and the essential oils of C. xanthorrhiza in admixture with a pharmaceutical carrier.

The carrier can be either solid pharmaceutical carrier or diluent, or liquid pharmaceutical carrier or diluent possibly in admixture with sweetening and/or flavoring agent when intended for oral administration.

The pharmaceutical composition according to the present invention can be utilized in any of the dosage forms conventionally used for oral administration.

As the dosage form suitable for oral administration, powder, tablets, pills, capsules and dragees may be mentioned as examples. The composition may be associated with a conventional carrier or diluent such as lactose, starch, calcium phosphate, talc, magnesium stearate, polyvinyl pyrrolidone, carboxymethylcellulose and gelatine.

A preferred composition for the soft capsule is the following: curcuminoids (10 mg), C. xanthorrhiza essential oil (25 mg), C. xanthorrhiza oil (25 mg), C. domestica essential oil (75 mg), C. domestica oil (75 mg), safflower oil (26.2 mg), cera alba (8 mg), hydrogenated soya oil (8 mg), vegetable shortening (32 mg), and aerosil (5.8 mg). Cera alba, purified from bee's wax, can be obtained from Fasting & Co., B.V., 2501 CE Den Haag, Postbus 226, Netherlands. Aerosil, colloidal silicon dioxide, can be obtained from Degussa, 6000 Frankfurt (Main) 1, P.O. Box 3993, West Germany. The vegetable shortening used is refined, hydrogenated vegetable oil obtained from PT Eresindo Jaya, Jakarta, Indonesia.

The liquid composition for oral administration may preferably be used in the form of syrup, emulsion or suspension, in which sweetening agent such as sucrose, fructose, glucose, mannitol, sorbitol, and/or flavoring agents such as cherry, fruit, orange, mint, may be added.

The preferred liquid composition for oral administration contains the following: essential oil of C. xanthorrhiza (25 mg), essential oil of C. domestica (75 mg), curcuminoids (10 mg), Ginger extract (200 mg), essential oil of Ginger (200 mg), sugar (7g), and extract of Tamarind sufficient for providing taste, all dissolved in 75 ml of water. Ginger (Zingiber offiale) extract is prepared by alcohol extraction of the dried rhizome in the same way curcumins are extracted from Curcuma. The extract is then steam distilled to obtain the essential oil of Ginger. The proportion of essential oils of C. domestica to essential oils of C. xanthorrhiza to curcuminoids is within a range of approximately 5-15:2-7.5:1, respectively. The best effect is found within the range of 7.5-10:2.5-5:1.

In the case of treating human beings, the average daily dose is between 0.25 g-0.50 g of the combination for adults weighing approximately 60 kg. The preferred dose is between 0.33-0.42 g.

The following examples are offered by way of example and are not to be construed as limitations in any way to the process described herein.

EXAMPLE 1

Preparation of Essential Oils

C. domestica or C. xanthorrhiza rhizomes are cut into slices, dried and powdered. 25 kilograms of the powder is mixed with 25 liters of petroleum ether (Pae) and allowed to stand overnight in a tightly sealed container. The Pae containing the essential oils is then pressed out under a pressure of about 400 atmospheres (atm) using a Hafico Tincture Press. This is repeated several times until no more oil can be extracted. The Pae is evaporated and the residue is steam distilled. The yield of essential oil using this technique is about 3-4% of the dry weight of the rhizome for C. domestica and about 8-10% for C. xanthorrhiza.

EXAMPLE 2

Preparation of Curcuminoids

The root residue after Pae extraction of the essential oils is used to prepare the curcuminoids. The root residue is extracted under the same conditions as above, but ethyl alcohol is substituted for Pae. After pressing out the alcohol several times in a Hafico Tincture Press, the alcohol is evaporated and the curcuminoids are recrystalized.

EXAMPLE 3

Separation of bis-desmethoxycurcumin from Other Curcuminoids

Separation of bis-desmethoxycurcumin was accomplished by flash chromatography using a silica gel column (230-400 mesh). First, benzene is used to elute most of the curcumin from the column. Next, a mixture of benzene and ethyl alcohol (99.5:1, respectively) is used to elute desmethoxycurcumin from the column. The bis-desmethoxycurcumin remains in the column after these two elution steps. The benzene and alcohol are then evaporated to recover the curcuminoids substantially free of bis-desmethoxycurcumin.

EXAMPLE 4

Comparison of the Anti-inflammatory Activity of Curcuminoids Alone, Essential Oils of C. domestica alone, the Essential Oils of C. xanthorrhiza alone, and the Combination of the Three.

Male inbred albino rats of the Wistar derived LMR strain, weighing between 140 and 160 grams are used. Each treatment group consists of ten rats. The rats are fasted for one night and weighed the next morning. Oedema is induced in the right-hind paw of each rat by means of an injection of 1% carrageenan solution. Before the injection and each hour after injection, the volume of the right-hind paw is measured. Measurement of the volume is done by dipping the rats paw into a liquid up to a predetermined mark and measuring or weighing the displaced liquid. The apparatus for measuring volume is calibrated against objects with known volumes.

Animals in the treatment groups are administered the drug orally once an hour for three hours before induction of oedema. Animals in the control groups are administered either safflower oil or polyethyleneglycol (PEG) one hour before induction. Piroxicam, a known anti-inflammatory agent used as a positive control, is administered one hour before induction.

The results are presented in Table 1.

TABLE I

| Dose | % Oedema Inhibition* over 6 Hr. Period After Induction | | | | | |
|---|---|---|---|---|---|---|
| | 1 hr. | 2 hr. | 3 hr. | 4 hr. | 5 hr. | 6 hr. |
| 3 × 0.1 g C. domestica essential oils | 21.5 | 22.8 | 7.0 | 2.6 | 7.0 | 7.2 |
| 3 × 0.1 g C. xanthorrhizn essential oils | 22.3 | 22.8 | 15.8 | 12.4 | 10.3 | 10.0 |
| 3 × 0.01 g Curcuminoids** | 16.5 | 17.6 | 14.9 | 10.2 | 9.5 | 11.9 |
| 3 × 0.11 g Combination*** | 19.8 | 52.3 | 47.4 | 40.0 | 32.4 | 28.6 |

TABLE I-continued

| Dose | % Oedema Inhibition* over 6 Hr. Period After Induction | | | | | |
|---|---|---|---|---|---|---|
| | 1 hr. | 2 hr. | 3 hr. | 4 hr. | 5 hr. | 6 hr. |
| 0.01 g Piroxicam | 25.9 | 49.0 | 52.6 | 43.4 | 41.4 | 36.5 |

*Calculated as: $\left(\dfrac{\text{volume of oedema in control group} - \text{volume of oedema in treatment group}}{\text{volume of oedema in control group}}\right) \times 100$ Volume in both treatment and control groups is average for 10 rats.
**Control group administered PEG, controls for other treatments administered safflower oil.
***0.075 g essential oil of C. domestica, 0.025 g essential oil of C. xanthorrhiza 0.01 g Curcuminoids

What is claimed is:

1. A method of treating inflammation in a patient by administering to the patient an effective dose of a pharmaceutical composition capable of treating the inflammatory condition, the composition comprising essential oils extracted from tissues of *Curcuma domestica* or *Curcuma xanthorrhiza* or a combination of both oils and curcuminoid substantially free of bis-desmethoxycurcumin.

2. A method of claim 1 wherein the proportion of essential oil of *C. domestica* to essential oil of *C. xanthorrhiza* to curcuminoid is within a range of approximately 5-15:2-7.5:1.

3. A method of claim 2 wherein the range of proportions is 7.5-10:2.5-5:1.

4. A method of claim 3 wherein the proportion of essential oil of *C. domestica* is about twice the proportion of *C. xanthorrhiza*.

5. A method of claim 1 wherein the pharmaceutical composition is administered via a dosage form suitable for oral administration.

6. A pharmaceutical composition comprising active ingredients of curcuminoid substantially free of bis-desmethoxycurcumin and essential oils extracted from tissues of *Curcuma domestica* or *Curcuma xanthorrhiza* or a combination of both oils and pharmaceutical carrier.

7. A composition of claim 6 wherein the proportion of essential oil of *C. domestica* to essential oil of *C. xanthorrhiza* to curcuminoid is within a range of approximately 5-15:2-7.5:1 respectively.

8. A composition of claim 7 wherein the range of proportions is 7.5-10:2.5-5:1.

9. A composition of claim 7 wherein the proportion of essential oil of *C. domestica* is about twice the proportion of *C. xanthorrhiza*.

10. A composition of claim 8 wherein the pharmaceutical carrier comprises pharmaceutical excipients suitable for oral administration.

11. A composition of claim 10 wherein the excipients are contained within a soft capsule.

12. A composition of claim 11 wherein the excipients comprise *C. xanthorrhiza* oil, *C. domestica* oil, safflower oil, cera alba, hydrogenated soya oil, vegetable shortening, and aerosil.

13. A composition of claim 10 wherein the excipients comprise a solution suitable for drinking.

14. A composition of claim 13 wherein the excipients comprise ginger extract, essential oil of ginger, sugar, and extract of tamarind.

* * * * *